(12) United States Patent
Barclay et al.

(10) Patent No.: US 6,974,473 B2
(45) Date of Patent: *Dec. 13, 2005

(54) FUNCTION-ENHANCED THROMBOLYTIC AV FISTULA AND METHOD

(75) Inventors: Bruce J Barclay, Cupertino, CA (US); Thomas J. Fogarty, Portola Valley, CA (US)

(73) Assignee: Vascular Architects, Inc., San Jose, CA (US)

( * ) Notice: Subject to any disclaimer, the term of this patent is extended or adjusted under 35 U.S.C. 154(b) by 562 days.

This patent is subject to a terminal disclaimer.

(21) Appl. No.: 10/180,564

(22) Filed: Jun. 26, 2002

(65) Prior Publication Data

US 2003/0028245 A1 Feb. 6, 2003

Related U.S. Application Data

(63) Continuation-in-part of application No. 09/910,703, filed on Jul. 20, 2001, and a continuation-in-part of application No. 09/740,597, filed on Dec. 19, 2000, which is a continuation-in-part of application No. 09/608,734, filed on Jun. 30, 2000, now Pat. No. 6,585,760.

(51) Int. Cl.[7] ............................................... A61F 2/06
(52) U.S. Cl. .................... 623/1.22; 623/1.13; 623/1.16
(58) Field of Search ............................. 623/1.13, 1.14, 623/1.22, 1.44–1.46, 1.15

(56) References Cited

U.S. PATENT DOCUMENTS

| | | | |
|---|---|---|---|
| 4,553,545 A | 11/1985 | Maass et al. | |
| 4,760,849 A | 8/1988 | Kropf | |
| 4,795,458 A | 1/1989 | Regan | |
| 5,007,926 A | 4/1991 | Derbyshire | |
| 5,123,917 A | 6/1992 | Lee | |
| 5,147,370 A | 9/1992 | McNamara et al. | |
| 5,282,823 A | 2/1994 | Schwartz et al. | |
| 5,399,352 A | 3/1995 | Hanson | |
| 5,419,760 A | 5/1995 | Narciso, Jr. | |
| 5,441,515 A | 8/1995 | Khosravi et al. | |
| 5,500,013 A | 3/1996 | Buschemi et al. | |
| 5,551,954 A * | 9/1996 | Buscemi et al. | 623/1.15 |
| 5,605,696 A | 2/1997 | Eury et al. | |
| 5,639,278 A | 6/1997 | Dereume et al. | |
| 5,676,685 A | 10/1997 | Razavi | |
| 5,683,451 A | 11/1997 | Lenker et al. | |
| 5,693,085 A * | 12/1997 | Buirge et al. | 623/1.13 |
| 5,700,285 A | 12/1997 | Myers et al. | |
| 5,728,751 A * | 3/1998 | Patnaik | 623/1.46 |
| 5,797,887 A | 8/1998 | Rosen et al. | |

(Continued)

FOREIGN PATENT DOCUMENTS

EP 0 893 108 A2 1/1999

(Continued)

OTHER PUBLICATIONS

D. Maass, Ch. L. Zollikofer, F. Largiader, and A. Senning, "Radiological Follow-up of Transluminally Inserted Vascular Endoprostheses: An Experimental Study Using Expanding Spirals," Radiology, 1984, vol. 152, No. 3, pp. 659-663.

(Continued)

Primary Examiner—Julian W. Woo
(74) Attorney, Agent, or Firm—James F. Hunn; Haynes Beffel & Wolfeld LLP

(57) ABSTRACT

A coiled stent graft, including a thrombolytic agent, is positionable within an AV fistula and optionally into one or both of the artery and the vein (6) to help reduce or eliminate blockages within the blood vessel at the junction between the AV fistula and the blood vessel.

35 Claims, 15 Drawing Sheets

U.S. PATENT DOCUMENTS

| | | | |
|---|---|---|---|
| 5,824,053 A | 10/1998 | Khosravi et al. | |
| 5,824,054 A | 10/1998 | Khosravi et al. | |
| 5,855,598 A | 1/1999 | Pinchuk | |
| 5,866,217 A | 2/1999 | Stenoien et al. | |
| 5,873,904 A | 2/1999 | Ragheb et al. | |
| 6,027,516 A | 2/2000 | Kolobow et al. | |
| 6,028,164 A | 2/2000 | Loomis | |
| 6,090,134 A | 7/2000 | Tu et al. | |
| 6,149,681 A | 11/2000 | Houser et al. | |
| 6,241,691 B1 * | 6/2001 | Ferrera et al. | 623/1.22 |
| 6,264,684 B1 | 7/2001 | Banas et al. | |
| 6,273,913 B1 | 8/2001 | Wright et al. | |
| 6,299,448 B1 | 10/2001 | Zdrahala et al. | |
| 6,306,166 B1 * | 10/2001 | Barry et al. | 623/1.46 |
| 6,309,413 B1 | 10/2001 | Dereume et al. | |
| 6,355,055 B1 * | 3/2002 | Waksman et al. | 623/1.13 |
| 6,358,276 B1 | 3/2002 | Edwin | |
| 6,585,760 B1 * | 7/2003 | Fogarty | 623/1.22 |
| 2001/0032010 A1 | 10/2001 | Sandock | |

FOREIGN PATENT DOCUMENTS

| | | |
|---|---|---|
| WO | WO 97/40755 | 11/1997 |
| WO | WO 98/47447 | 10/1998 |

OTHER PUBLICATIONS

Albert W. Chan, MD, MSc, Derek P. Chew, MBBS, and A. Michael Lincoff, MD, "Update on Pharmacology for Restenosis," Current Interventional Cardiology Reports 2001, 3:149-155, Current Science Inc., Cleveland, OH, USA.

"Applications of Nanoporous Gold Explored," News & Analysis.

"DOE Researchers Developing Polymer Gel for Medical Applications," News & Analysis, Medical Device & Diagnostic Industry, May 2001.

Aruny et al., "Quality Improvement Guidelines for Percutaneous Management of the Thrombosed or Dysfunctional Dialysis Access," JVIR, 10:491-498 (1999).

Coulson et al., "A Combination of the Elephant Trunk Anastomosis Technique and Vascular Clips for Dialysis Grafts," Surgical Rounds, pp. 596-608 (Nov. 1999).

Gray et al., "Reporting Standards for Percutaneous Interventions in Dialysis Access," JVIR, 10(10):1405-1415 (1999).

Kohler et al., "Dialysis access failure: A sheep model of rapid stenosis," J Vasc. Surg., 30:744-751 (1999).

Kohler, Ted R., "Intimal Hyperplasia—Endothelial Cell Biology," from the Seventh Biannual Symposium on Dialysis Access, Vascular Access for Hemodialysis VII, pp. 1-2 (May 2000).

Martin et al., "Prophylactic Angioplasty Reduces Thrombosis in Virgin ePTFE Arteriovenous Dialysis Grafts with Greater than 50% Stenosis: Subset Analysis of a Prospectively Randomized Study," JVIR, 10:389-396 (1999).

Polo, Jose R., "The State of the Art of Surgical Treatment for Failing Grafts," from the Seventh Biannual Symposium on Dialysis Access, Vascular Access for Hemodialysis VII, pp. 8-9 (May 2000).

Vesely, Thomas M., "the State of the Art of Radiologic Intervention," from the Seventh Biannual Symposium on Dialysis Access, Vascular Access for Hemodialysis VII, pp. 4-7 (May 2000).

* cited by examiner

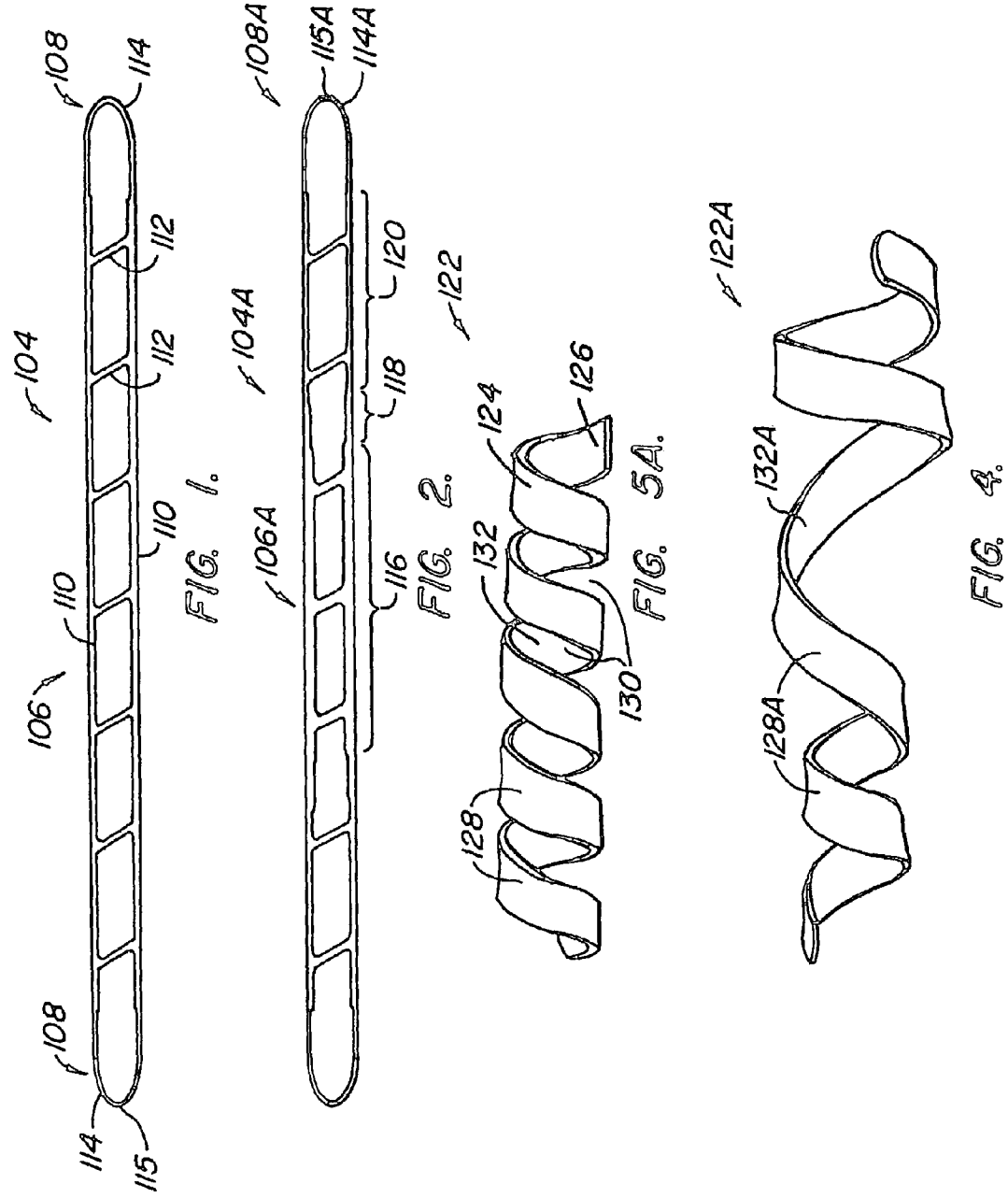

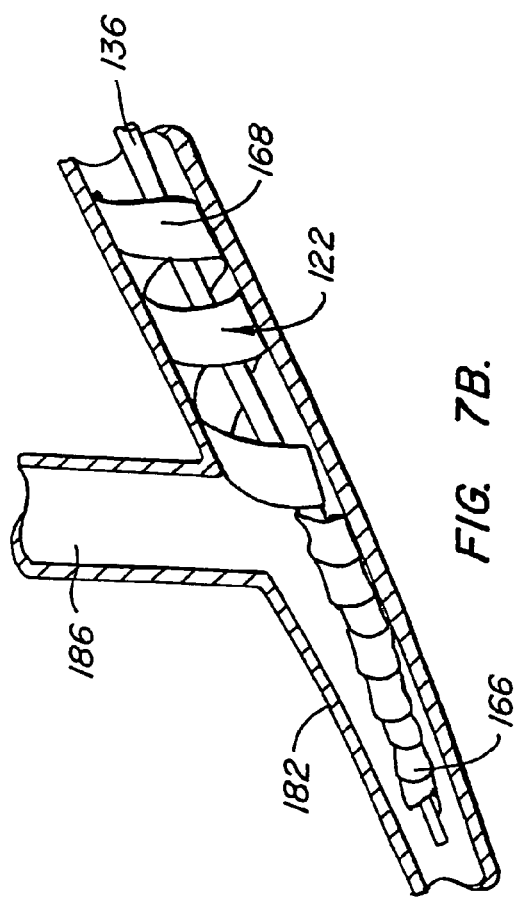
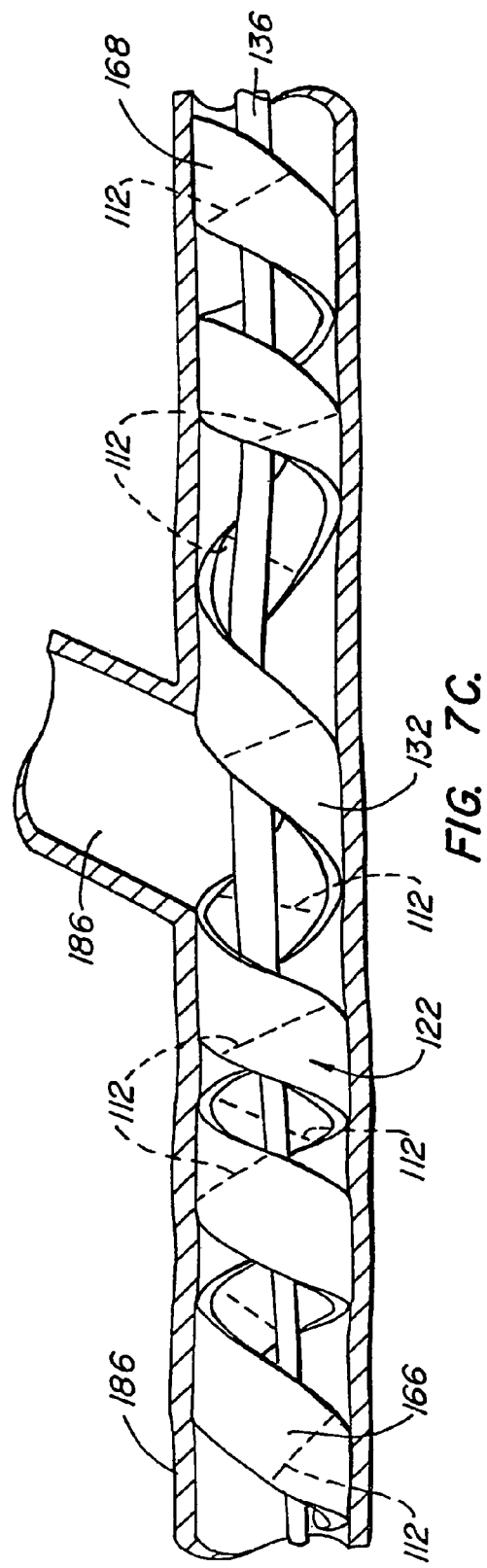
FIG. 7B.
FIG. 7C.

US 6,974,473 B2

FUNCTION-ENHANCED THROMBOLYTIC AV FISTULA AND METHOD

CROSS-REFERENCE TO OTHER APPLICATIONS

This is a continuation in part of U.S. patent application Ser. No. 09/608,734 filed Jun. 30, 2000 now U.S. Pat. No. 6,585,760, and U.S. patent application Ser. No. 09/910,703 filed Jul. 20, 2001, which is a continuation in part of U.S. patent application Ser. No. 09/740,597 filed Dec. 19, 2000. U.S. patent application Ser. No. 09/910,703 incorporates by reference the following U.S. Pat. No. 6,248,122 B1 issued Jun. 19, 2001; U.S. Pat. No. 6,238,430 B1 issued May 29, 2001; U.S. patent application Ser. No. 09/400,955 filed Sep. 22, 1999; and U.S. patent application Ser. No. 09/608,281 filed Jun. 30, 2000.

BACKGROUND OF THE INVENTION

A fistula is an abnormal passage typically between two organs, such as an artery and a vein. An arterio-venous (AV) fistula is a natural or an artificial graft, typically made of ePTFE (expanded PTFE), between a vein and an artery. An AV fistula, as used herein, also includes naturally-occurring native tissue tubular connections between a vein and an artery. AV fistulas are often used to provide multiple needle access sites for hemodialysis. The AV fistula also helps to increase blood flow through the vein to accommodate the flow rate of blood needed for hemodialysis.

One problem associated with AV fistulas is the progressive narrowing of the AV fistula at the junction with the vein. Such obstructions occur when vascular muscle cells begin growing inwardly causing, for example, thrombosis within the AV fistula. When the thrombus becomes sufficiently large, blood flow decreases and the AV fistula ceases to be effective. It has been found that graft patency after six months is only 66% and that graft failure occurs, on the average, after 18 months.

Improved graft patency has been achieved by the use of vascular clips instead of suturing the AV fistula to the vein. Variations in the angle of implantation have also been shown to affect AV fistula patency. The use of a short length of a PTFE graft has been inserted in the vein to improve patency. (A. S. Coulson, et al., A Combination of the Elephant Trunk Anastomosis Technique and Vascular Clips for Dialysis Grafts, Surgical Rounds, 596–608, November 1999.) Also, a PTFE bypass graft to a proximal dilated vein has been used in response to the occurrence of graft-vein stenosis. (Polo, J. R., The State of the Art of Surgical Treatment for Failing Grafts, The Seventh Biannual Symposium on Dialysis Access—Vascular Access for Hemodialysis VII, pp.8–9, May 2000.) Balloon angioplasty and endovascular stents may be used to treat stenosis in AV fistulas (J. E. Aruny, et al., Quality Improvement Guidelines for Percutaneous Management of the Thrombosed on Dysfunctional Dialysis Access, JVIR, 10:491–498, April 1999.) However, there still exists the need to stop, or at least slow, the obstruction of the AV fistula to prolong the patency of the graft.

An endoluminal prosthesis typically comprises at least one radially expansible, usually cylindrical, body segment. By "radially expansible," it is meant that the body segment can be converted from a small diameter configuration (used for endoluminal placement) to a radially expanded, usually cylindrical, configuration which is achieved when the prosthesis is implanted at the desired target site. The prosthesis may be non-resilient, e.g., malleable, thus requiring the application of an internal force to expand it at the target site. Typically, the expansive force can be provided by a balloon catheter, such as an angioplasty balloon for vascular procedures. Alternatively, the prosthesis can be self-expanding. Such self-expanding structures may be provided by a temperature-sensitive superelastic material, such as Nitinol, which naturally assumes a radially expanded condition once an appropriate temperature has been reached. The appropriate temperature can be, for example, a temperature slightly below normal body temperature; if the appropriate temperature is above normal body temperature, some method of heating the structure must be used. Another type of self-expanding structure uses resilient material, such as a stainless steel or superelastic alloy, and forming the body segment so that it possesses its desired, radially-expanded diameter when it is unconstrained, e.g., released from radially constraining forces of a sheath. To remain anchored in the body lumen, the prosthesis will remain partially constrained by the lumen. The self-expanding prosthesis can be delivered in its radially constrained configuration, e.g. by placing the prosthesis within a delivery sheath or tube and retracting the sheath at the target site. Such general aspects of construction and delivery modalities are well-known in the art.

One type of endoluminal prosthesis includes both a stent component and a graft-type covering component. These endoluminal prostheses are often called stent grafts. A stent graft is typically introduced using a catheter with both the stent and graft in contracted, reduced-diameter states. Once at the target site, the stent and graft are expanded. After expansion, the catheter is withdrawn from the vessel leaving the stent graft at the target site. Grafts may be made of, for example, PTFE, ePTFE or Dacron® polyester.

It has been found effective to introduce pores into the walls of the graft to provide in growth of tissue onto the walls of the graft. With larger diameter grafts, woven graft material is often used. In small and large diameter vessels, porous fluoropolymers, such as ePTFE, have been found useful.

Coil-type stents can be wound about the catheter shaft in torqued compression for deployment. The coil-type stent can be maintained in this torqued compression condition by securing the ends of the coil-type stent in position on a catheter shaft. The ends are released by, for example, pulling on wires once at the target site. See, for example, U.S. Pat. Nos. 5,372,600 and 5,476,505. Alternatively, the endoluminal prosthesis can be maintained in its reduced-diameter condition by a sleeve; the sleeve can be selectively retracted to release the prosthesis. A third approach is the most common. A balloon is used to expand the prosthesis at the target site. The stent is typically extended past its elastic limit so that it remains in its expanded state after the balloon is deflated and removed. One balloon expandable stent is the Palmaz-Schatz stent available from the Cordis Division of Johnson & Johnson. Stents are also available from Medtronic AVE of Santa Rosa, Calif. and Guidant Corporation of Indianapolis, Ind.

SUMMARY OF THE INVENTION

As used herein, biologically active agents include diagnostic and therapeutic agents, such as radiation-emitting agents used for imaging and/or therapy; compounds used to help prevent restenosis such as anti-inflammatory drugs, anti-thrombotic/anti-platelet drugs, and anti-proliferative drugs; apoptosis drugs; and light-activated drugs that intercalate into DNA or RNA strands (8-methoxypsoralen), cross-link into DNA or RNA strands (8-methoxysporalen plus UV light), or cause apoptosis (phthalocynine) or necrosis tin ethyl etiopurpurin) when activated with light. The following are examples of several of these groups of agents.

Anti-Inflammatory Drugs:
Aspirin or acetyl salicylic acid
Oral Corticosteroids (generic name followed by trademark in parentheses)—Prednisone (Deltasone), methylprenisolone (Medrol), prednisolone solution (Pediapred, Prelone)
Inhaled Corticosteroids (generic name followed by trademark in parentheses)—Flunisolide (AeroBid, AeroBid-M), triamcinolone (Azmacort), beclomethasone (Beclovent, Vanceril), budesonide (Pulmicort), fluticasone (Flovent), Nedocromil sodium (Tilade), Cromolyn sodium (Intal)

Nonsteroidal Anti-inflamatory Agents (Generic Names):
1. Diclofenac
2. Diflunisal‡
3. Etodolac †
4. Fenoprofen‡
5. Floctafenine *
6. Flurbiprofen ‡§
7. Ibuprofen ‡§
8. Indomethacin‡
9. Ketoprofen ‡
10. Meclofenamate †‡
11. Mefenamic Acid
12. Meloxicam ‡
13. Nabumetone
14. Naproxen ‡
15. Oxaprozin
16. Phenylbutazone ‡
17. Piroxicam ‡
18. Rofecoxib
19. Sulindac ‡
20. Tenoxicam *
21. Tiaprofenic Acid *
22. Tolmetin (‡
* Not commercially available in the U.S.
† Not commercially available in Canada
‡ Generic name product may be available in the U.S.

Anti-Thrombotic Drugs (Generic Names):
Anisindione Indications: Embolism, pulmonary; Embolism, pulmonary, prophylaxis; Thrombosis; Thrombosis, prevention
Antithrombin III (Human) Indications: Embolism; Thrombosis
Argatroban Indications: Thrombosis; Thrombocytopenia, secondary to heparin
Dicumarol Indications: Embolism, pulmonary; Embolism, pulmonary, prevention; Fibrillation, atrial, adjunct; Occlusion, coronary, adjunct; Thrombosis; Thrombosis, prevention
Heparin Sodium Indications: Coagulopathy, consumption; Dialysis, adjunct; Embolism, pulmonary; Embolism, pulmonary, prevention; Fibrillation, atrial, adjunct; Surgery, adjunct; Thrombosis; Thrombosis, prevention; Transfusion, adjunct
Lepirudin (rDNA) Indications: Thrombocytopenia, secondary to heparin; Thrombosis tPA, Reteplase (generic for Retavase®), Urokinase Anti-Proliferative Drugs (Generic Name Followed by Trademark in Parentheses):

Terazosin—(Hytrin) Antihypertensive, Benign prostatic hyperplasia therapy agent
Finasteride (Systemic)—(Propecia, Proscar) Benign prostatic hyperplasia therapy agent; hair growth stimulant, alopecia androgenetica (systemic)
Doxazosin (Systemic)—(Cardura) Antihypertensive, Benign prostatic hyperplasia therapy agent
Tamsulosin (Systemic)—(Flomax) Benign prostatic hypertrophy therapy agent
Prazosin (Systemic)—(Minipress) Antidote, to ergot alkaloid poisoning, Antihypertensive, Benign prostatic hyperplasia therapy agent, Vasodilator, congestive heart failure, Vasospastic therapy adjunct More examples of anti-proliferative drugs (generic name followed by trademark name in parentheses): Mitomycin for injection (Mutamycin); bleomycin sulfate for injection (Blenoxane); doxorubicin hydrochloride for injection (Adriamycin or Rubex or Doxorubicin hydrochloride); daunorubicin HCl (Cerubidine); dactinomycin for injection (Cosmegen); daunorubicin citrate (liposome) for injection (DaunoXome); doxorubicin HCl (liposome) for injection (Doxil), epirubicin hydrochloride for injection (Ellence); idarubicin hydrochloride for injection (Idamycin); plicamycin (Mithracin); pentostatin for injection (Nipent); mitoxantrone for injection (Novantrone); and valrubicin (Valstar).

The present invention is directed to a thrombolytic AV fistula assembly and a method for enhancing the function of an AV fistula to help reduce any thrombosis associated therewith.

A first aspect of the invention is directed to an AV fistula function enhancing method including selecting an endoluminal prosthesis including a coiled body and a graft material covering at least part of the coiled body to create a coiled stent graft. The selecting step includes choosing an endoluminal prosthesis carrying a thrombolytic agent. The stent graft is placed within the AV fistula and optionally within at least one blood vessel to which the AV fistula is connected. The thrombolytic agent helps to reduce any thrombosis associated with the stent graft. The use of the AV fistula helps to prevent, or at least retard, the obstruction of the AV fistula by eliminating, or at least reducing, the accumulation of matter in the AV fistula. Other biologically-active agents, such as anti-restenotic agents, may also be used.

Another aspect of the invention is directed to a thrombolytic AV fistula assembly, including an AV fistula having a tubular body and a coiled stent graft housable at least partially within the AV fistula and at least one of the venous and arterial ends. The coiled stent graft includes a coiled body, a graft material at least partially covering the coiled body and a thrombolytic agent, the thrombolytic agent helping to reduce any thrombosis associated with the stent graft.

The turns of the stent graft at the vein/AV fistula junction may be spaced apart from one another so to insubstantially or partly hinder fluid flow along the vein. The turns of the stent graft may also be such as to effectively block fluid flow along the vein.

Other features and advantages of the invention will appear from the following description in which the preferred embodiments have been set forth in detail in conjunction with the accompanying drawings.

BRIEF DESCRIPTION OF THE DRAWINGS

FIG. 1 illustrates a stent blank used to create a coiled stent such as those shown in FIGS. 3, 4 and 5A.

FIG. 2 illustrates a stent blank similar to that of FIG. 1 but having different thicknesses along its length;

FIG. 4 illustrates a stent graft similar to that of FIG. 3 but in which one end of the stent graft has much greater radially expanded diameter than the other portion to accommodate a vessel having different internal diameters;

FIG. 5A shows a stent graft similar to that of FIG. 3 but with generally evenly-spaced turns;

FIG. 7B illustrates the release of the proximal half of the stent graft;

FIG. 7C illustrates the release of the distal half of the stent graft prior to the removal of the catheter shafts;

DESCRIPTION OF THE SPECIFIC EMBODIMENTS

Figure 3:
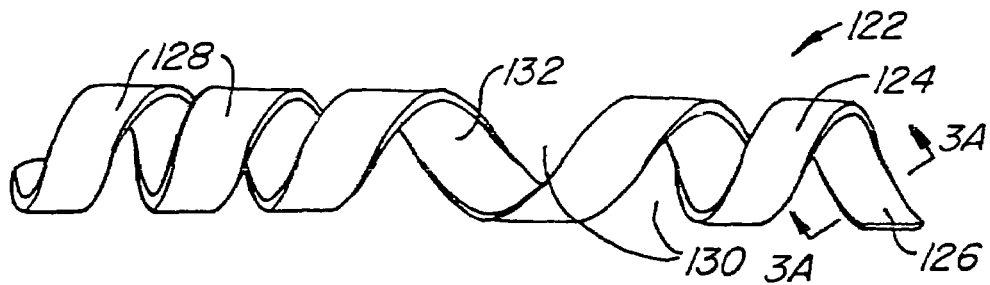
FIG. 3 illustrates a stent graft in a radially expanded condition, the stent graft including a stent similar to that shown in FIG. 1 covered with a sleeve of porous graft material, the stent graft having a central turn with a greatly increased pitch for placement at a branching intersection.

FIG. 1 illustrates a stent blank 104 used to create a coiled stent similar to that shown in FIGS. 3, 4 and 5A. Stent blank 104 includes a main body portion 106 and first and second end portions 108. Main body portion 106 includes side edge or rail elements 110 connected by connector or rung elements 112 to define openings 113 therethrough. Rung elements 112 are, as shown in FIG. 1, at an angle to rail elements 110 so that when stent blank 104 is formed into a coiled stent and tightly wrapped about an introducer catheter, such as in FIG. 7A, rung elements 112 are axially-extending so that they lie flat for a tighter wrap.

End portions 108 are thinner and thus more flexible than main body portion 106. In addition, end portions 108 have an inwardly tapering portion 114 terminating at a blunt tip 115. The shape of end portions 108 and the lessened stiffness of the end portions, compared to body portion 106, help to prevent tissue trauma during use. This type of coiled stent in which the end portions 108 are less stiff than the main body portion 106 can find particular utility in stabilizing a traumatic injury site within a patient, such as in the case of a dissection, flap or false lumen. End portion 108 could also be stiffer than main body portion; this embodiment may be useful, for example, when treating occlusive disease on either side of a branch vessel.

FIG. 2 illustrates a stent blank 104A similar to stent blank 104 of FIG. 1 but in which main body portion 106A has three different radial stiffness. That is, main body portion 106A has a first, central longitudinal section 116 of a first, greater stiffness, and second and third longitudinal sections 118, 120 on either side of first section 116. Sections 118, 120 are successively thinner and thus have successively lower radial stiffnesses when stent blank 104A is formed into a coiled stent. End portion 108A acts as the fourth longitudinal section with the least radial stiffness of any of the sections in this embodiment. Instead of a set of generally discrete radial stiffnesses, the radial stiffness could vary continuously along at least part of the length of stent blank 104A, and then along the resulting stent body.

In addition to providing less traumatic end portions 108, 108A, a coiled prosthesis formed from either of stent blanks 104, 104A, when uncoiling, will have a tendency to open up first in the center, because of the greater stiffness at the center, followed by the ends. This helps to reduce the degree to which the end portions 108, 108A are dragged along the surface of the vessel or other hollow body structure as the prosthesis is released.

FIGS. 1A–1D illustrate four different designs of stent blanks 104B–104E. Each of these different stent blanks has at least three rail elements 110 with connector or rung elements 112 extending between the rail elements. In the FIGS. 1A–1C embodiments connector elements 112 are aligned while in the 1D embodiment they are offset. The angles of connector elements 112 are such that when the stent blanks are formed into a tight coil during introduction, connector elements 112 are generally axially extending so they lie flat for a tighter wrap. FIG. 1E illustrates a coiled stent 105C made from stent blank 104C with one or more radiopaque markers 121 used to facilitate deployment. Stent blanks 104B–104E are relatively wide so to increase the radial force the coiled stents can apply to the walls of the hollow body organ within which they are to be placed. It has been found that reducing the number of turns for a stent graft having the same axial length helps to increase the user's control of the stent graft during placement. This is important in certain situations, such as when treating a dissection, in particular a vascular dissection such as the aortic dissection shown in FIG. 11 and discussed below. Also, as discussed above, the ends of stent blanks 104B–104E may be rounded or thinned in shape to cause a reduction in the radial force applied at the ends of the stent to help prevent vessel deformation at the ends of the stent.

When the stent blank is coiled, to act as the body of a coiled prosthesis, as illustrated in FIGS. 3–5C, the openings 113 in the stent are radially extending openings as illustrated in FIG. 1E. While openings 113 are shown as generally quadrilateral openings, they may be of other shapes, such as oval or circular or octagonal with a combination of straight and curved sides.

Figure 3A:
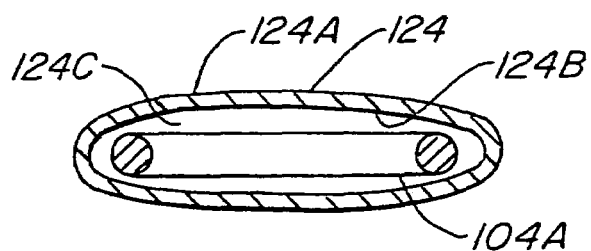
FIG. 3A is an enlarged cross-sectional view of a prosthesis taken along line 3A—3A of FIG. 3.

FIGS. 3, 4, 5 and 5A illustrate four stent graft embodiments 122, 122A, 122B, 122C. Stent graft 122 includes a ladder-type coiled stent formed from stent blank 104 and covered with tubular graft material 124. That is, graft material 124, see FIG. 3A, acts as a sleeve of material having an outer surface 124A and an inner surface 124B, the inner surface defining a sleeve interior 124C housing the entire stent 104A. Graft material 124 is preferably porous PTFE or ePTFE or Dacron® polyester. The ends 126 of graft material 124 are sealed, or for example, by using an adhesive or by placing a suitable heat seal material, such as FEP (fluorinated ethylene propylene) or other thermoplastic materials, between the layers of the graft material 124 and applying heat and pressure. The porous nature of the graft material permits sealing in this manner in spite of the inert nature of PTFE. In addition, a direct bond of the PTFE to itself, via a process known as sintering, may be employed. Other methods for sealing ends 126 could also be used. One or both of outer and inner surfaces 124A, 124B may be coated or graft material 124 may be otherwise treated to make the surface substantially impervious to the passage of blood therethrough. While it is presently preferred that graft material 124 completely enclose the stent, graft material may be a single layer and extend along a coiled path along only one side of the coiled body of the stent.

Figure 3B:
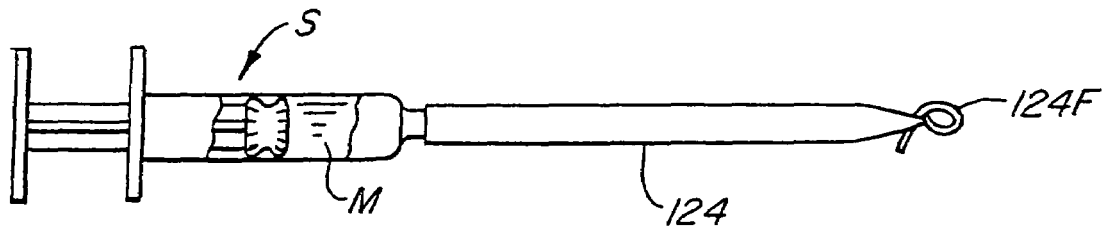
FIG. 3B is a simplified side view illustrating the introduction of a mixture of a carrier and a biologically active agent into the interior of a sleeve of a porous graft material.

The stent grafts of FIGS. 3–5C may be constructed for delivering a biologically active agent, if desired. Such covered, coiled drug delivery stents may be constructed in several ways. One way is to place one or more biologically active agents on one or both of outer and inner surfaces 124A, 124B of the sleeve of material 124 shown in FIG. 3A. A biologically active agent may also be on inner surface 124B or contained within sleeve interior 124C; such agent may be, for example, coated on the stent or may be captured between the stent and inner surface 124B. Another way is to incorporate the agent into graft material 124 to create an agent/material matrix. Such a matrix may be created by using a porous material for graft material 124. The porous graft material is then saturated with a mixture of a carrier, such as water or alcohol, and one or more agents. One way to do so is shown in FIG. 3B. A sleeve of graft material 124 has one end 124F knotted to close off that end while a syringe S is used to fill graft material 124 with the mixture M. When the mixture has fully saturated graft material 124, which is typically evident when the mixture seeps through the pores of graft material 124, the excess amounts of the mixture is drained and the now agent-laden graft material is at least partially dried. Another method is to manufacture the graft material with one or more agents interspersed therein. The agents may be, for example, microencapsulated to provide a time-release function for the agent. Time release may also be achieved by coating outer surface 124A with an appropriate biodegradable material.

Another way to deliver a biologically active agent will be described with reference to FIGS. 5D–5I. FIGS. 5D–5I are greatly enlarged cross-sectional views taken through covered, coiled drug delivery stents 145–145E. FIG. 5D illustrates a stent wall 139, having an outer surface 139A, covered by a porous covering 141, the porous covering covered by a protective coat 143. The porous covering, in this embodiment, is made of a porous covering/drug matrix, preferably using EPTFE as the porous covering. Protective coat 143 is preferably a biodegradable polymer. When the covered, coiled drug delivery stent 145 is in place within a patient, protective coat 143 begins to degrade so that after a period of time, the drug begins migration from the matrix to the patient.

Figure 5:
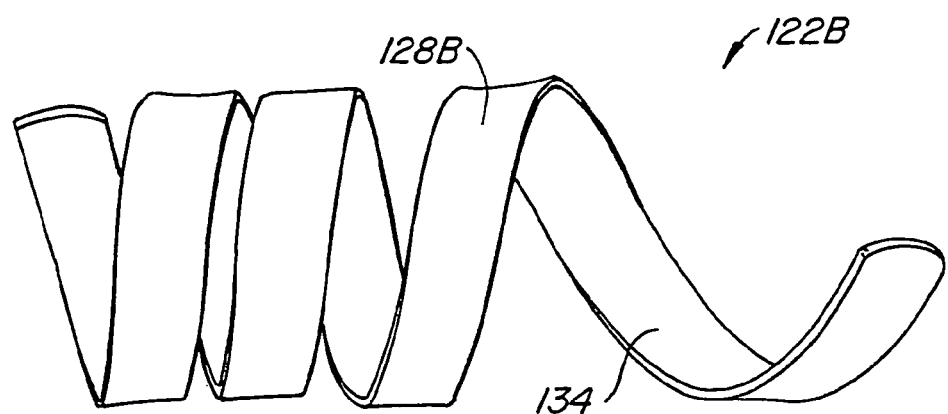
FIG. 5 illustrates an alternative embodiment to the stent graft of FIG. 3 in which the stent graft has a large expanded diameter and also has the one turn with the greater pitch at one end of the stent graft.
Figure 5B:
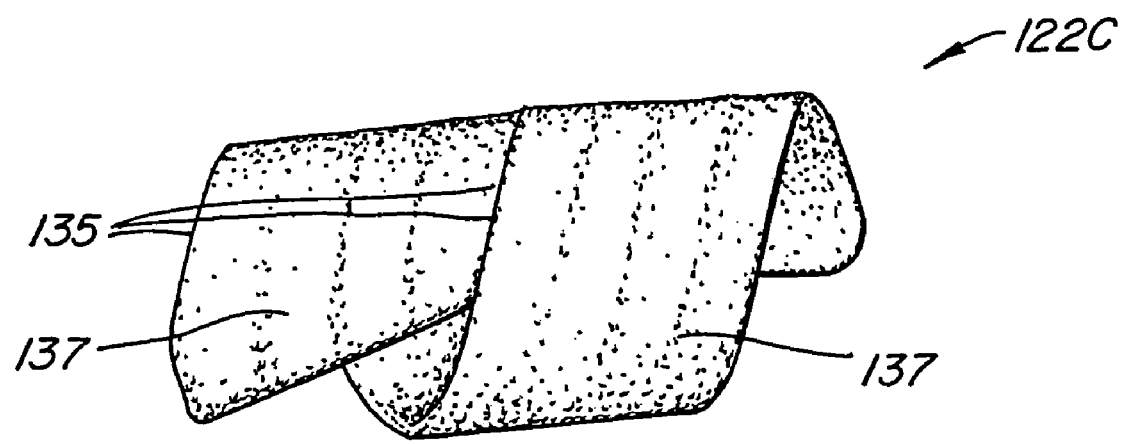
FIGS. 5B and 5C illustrate stent grafts made from the stent blank of FIG. 1C.
Figure 5C:
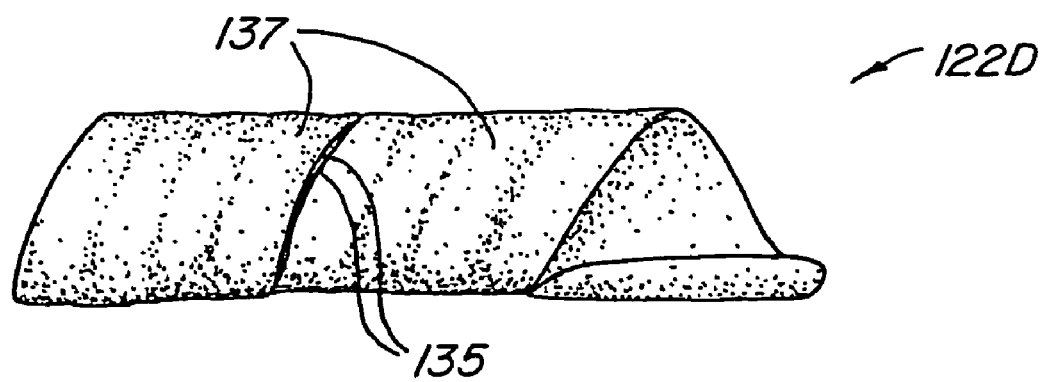
Figure 5D:
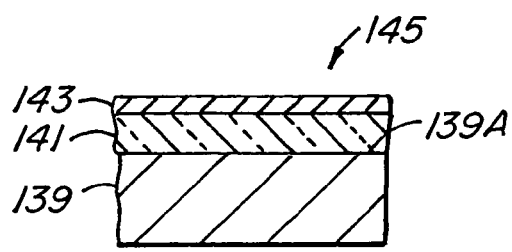
FIGS. 5D–5I are three enlarged, partial cross-sectional views of three different covered, coiled drug-delivery stents.
Figure 5G:
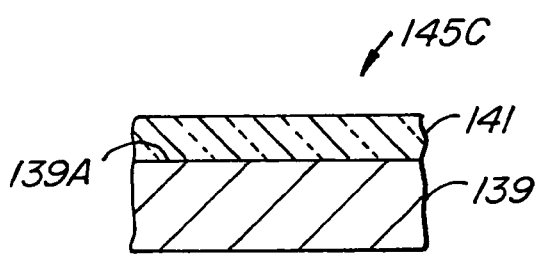
Figure 5E:
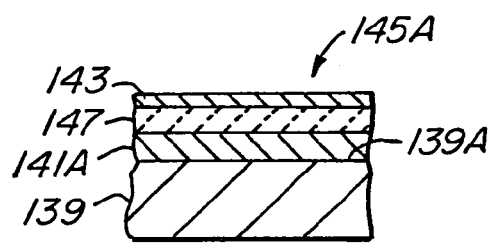
Figure 5H:
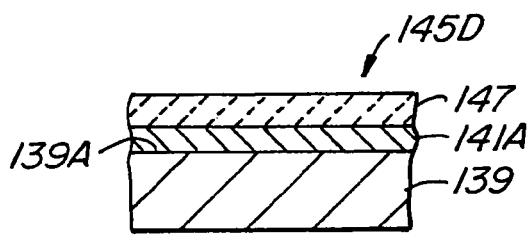
Figure 5F:
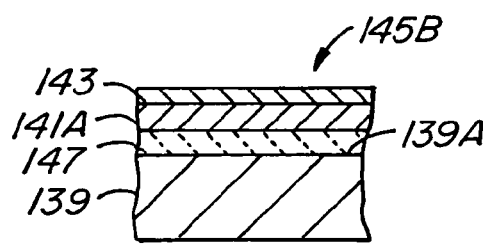
Figure 5I:
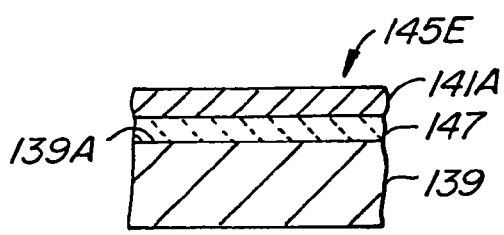

FIG. 5E discloses a further embodiment of the covered, coiled drug-delivery stent 145A, with like references referring to like elements. Porous covering 141 A in the embodiment of FIG. 5E is made of ePTFE, covered by a drug layer 147, which in turn is covered by protective coat 143. In the FIG. 5F embodiment, the arrangement of porous covering 141A and drug layer 147 is reversed from that of FIG. 5E so that drug layer 147 is between stent wall 139 and porous covering 141 A. In each of these situations, the drug is permitted to migrate from the stent 145, 145A, 145B, for interaction with the patient after the protective coat 143 has sufficiently degraded to expose the drug. Porous covering 141 is sufficiently porous to permit the drug to pass therethrough in the embodiments of FIGS. 5D and 5F. FIGS. 5G, 5H and 5I illustrate embodiments similar to FIGS. 5D, 5E and 5F but with protective coat 143 removed.

Drug layer 147 may include various types of therapeutic and diagnostic pharmaceuticals including, for example, NO generators, paclitaxel, statins, taxol, heparin in its various forms, i.e., low molecular weights, thienopyridines, glycoprotein IIb/IIIb inhibitors, antiplatelet agents, fibrinolytics, anticoagulants, thrombolytics, abciximab, rapamycin, hirudin, VEGF, Hirulog, ticlopidine and clopidogrel, as well as the biologically active agents listed above. Stents 145, 145A or 145B are made to deliver drug to the patient by directing the drug delivery stent to a target site within the patient, waiting for a protective material, initially shielding the drug, to be effectively removed from the stent, thereby exposing the drug. This is followed by permitting the drug to migrate from the stent for interaction with the patient.

In some situations it may be desirable to make the prosthesis in manner so that at least first and second biologically active agents are carried by the prosthesis and released in a manner so that at least some of the first agent, for example at least half, is released prior to the start of the release of the second agent. This can be accomplished in several ways. A protective coat 143 may be placed between layers of the biologically active agent. The first agent may be applied over the second agent to cover, and thus initially prevent the release of, the second agent. One or both of the agents may be encapsulated in biodegradable coverings so to be released only after a period of time.

Coiled stent graft 122 includes a number of spaced apart turns 128 defining a generally helical gap 130 therebetween. The average width of helical gap 130 is equal to about 0% to 1200% of the average width of turns 128. For some applications the average width of gap of 130 is about 50% to 800% of the average width of turns 128 when stent graft 122 is deployed. For other applications, such as placement at dissections discussed below, gap 130 is closed, that is about 0%.

Stent graft 122 has a generally constant pitch except at its central region. The pitch of a central turn 132 of stent graft 122 is substantially greater than the pitch of its adjacent turns 128 to accommodate placement of stent graft 122 at the intersection of a main or first vessel and a branching vessel as will be discussed in more detail with reference to FIGS. 7A–7C.

FIG. 4 illustrates a stent graft 122A in which a central turn 132A also has an increased pitch as opposed to adjacent turns 128A. However, the turns on one side of central turn 132A have a larger fully-expanded diameter than turns on the other side to accommodate transition between smaller and larger diameter vessels.

FIG. 5 illustrates a stent graft 122B designed for placement with the end turn 134 having a substantially greater pitch than its adjacent turn 128B. Stent graft 122B is used when one end of the stent graft is to be positioned at the intersection of main and branching vessels so that the stent graft extends to one side of the intersection as opposed to both sides as in the embodiments of FIGS. 3 and 4. FIG. 5A illustrates stent graft 122C, which may be used at locations other than bifurcations, having generally uniformly spaced turns 128C.

Figure 1A:
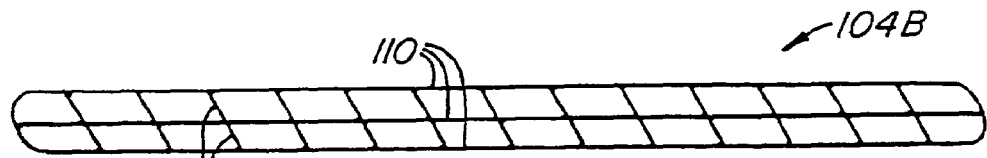
FIGS. 1A–1D illustrate four additional designs of stent blanks.
Figure 1B:
Figure 1C:
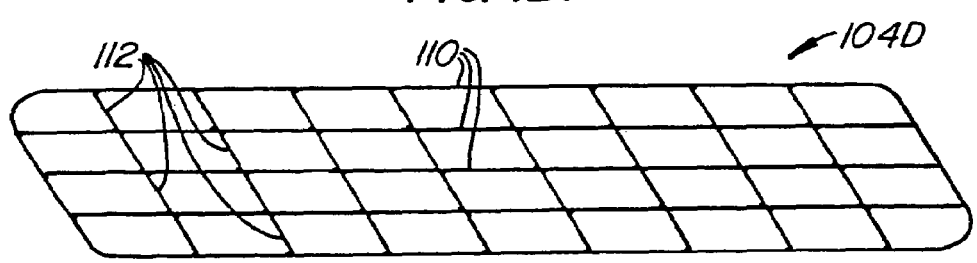
Figure 1D:
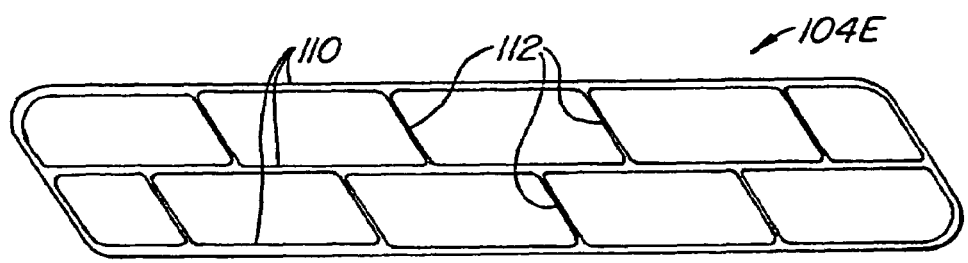
Figure 1E:
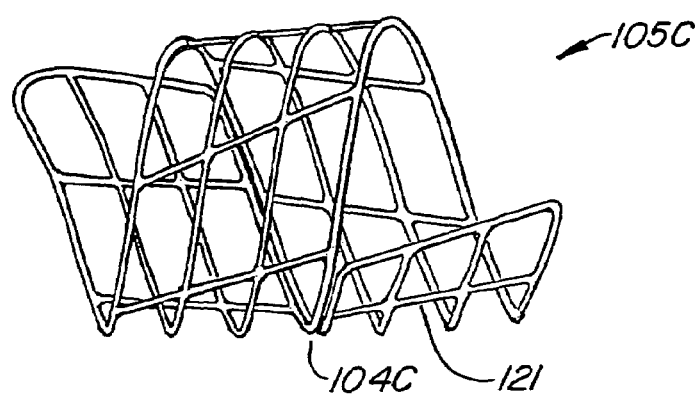
FIG. 1E shows a coiled stent made from the stent blank of FIG. 1B.

FIGS. 5B and 5C illustrate stent grafts 122C, 112D each made from stent blank 104D of FIG. 1C. Stent grafts 122C, 122D are designed and intended to have the edges 135 of adjacent turns 137 adjacent to one another. Such stent grafts as FIGS. 5B and 5C are intended for use in treating aortic dissections. The combination of having the width of each turn being relatively wide compared to the diameter when in the radial expanded condition, plus the use of abutting or overlapping adjacent edges, combine to make such a stent graft useful when full surface coverage and reasonably higher outward radial force are desired. The width of turns 137 is measured perpendicular to edges 135. Also, fewer turns can make the stent graft easier to control and require fewer rotations of shafts 138, 142 prior to release from catheter 136. Stent grafts 122C, 122D may be characterized by having an average diameter to turns-width ratio, when in their radially expanded conditions, from about 0.1 to 1 to about 2.4 to 1. Stent grafts 122C, 122D may also be characterized by having an average turns-width to stent graft length ratio, when in their radially expanded conditions, from about 1 to 1 to about 1 to 4. In some situations it may not be necessary or desired to have connectors 112 be axially extending when in the tightly wound, radially contracted condition. In some cases connectors 112 could be replaced by other shapes of connectors, such as wave- or undulating-shaped connectors, v-shaped connectors, x-shaped connectors, etc.

Figure 6A:
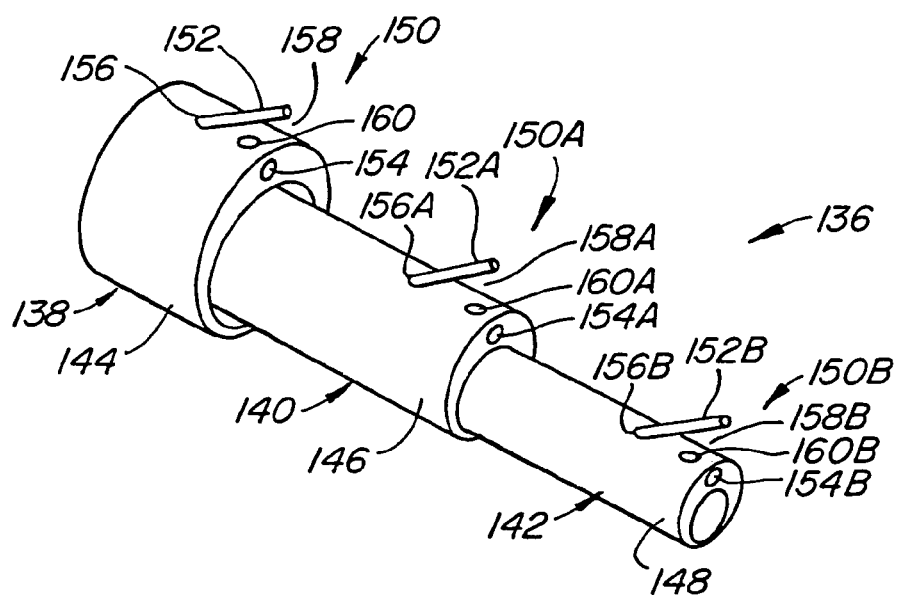
FIG. 6A is an overall view of the distal end of a three-shaft deployment catheter used to deploy the stent grafts of FIGS. 3–5.
Figure 6B:
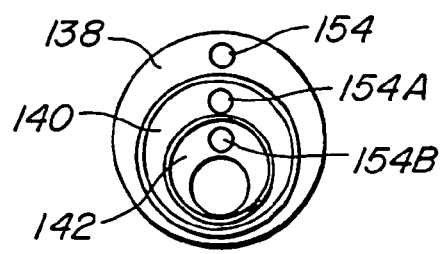
FIG. 6B is an end view of the shafts of 6A.
Figure 7A:
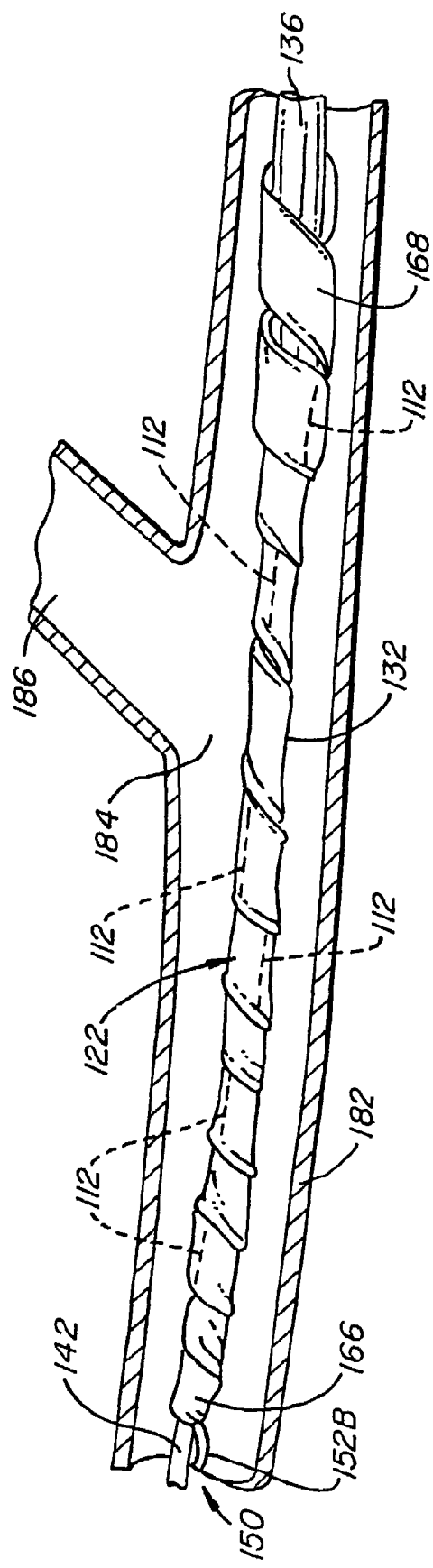
FIG. 7A illustrates the stent graft of FIG. 3 tightly wrapped about the distal end of the catheter of FIGS. 6A and 6B and placed within a vessel with the intermediate portion of the stent graft at the intersection of the main and branching vessels.

FIGS. 6A–6B illustrate a catheter 136 used for deploying the stent grafts of FIGS. 3 and 4. Catheter 136 includes outer, intermediate and inner rotating, telescoping shafts 138, 140, 142 each having a distal end 144, 146, 148. Each of the shafts has a prosthesis portion holder 150, 150A, 150B at its distal end 144, 146, 148. Prosthesis portion holders 150, 150A, 150B include pull wires 152, 152A, 152B which pass along axially-extending lumens 154, 154A, 154B formed in the body of shafts 138, 140, 142, out of exit holes 156, 156A, 156B, across gaps 158, 158A, 158B and back into reinsertion openings 160, 160A, 160B. Pull wires 152, 152A, 152B pass through and engage different portions of, for example, stent graft 122 and secure those portions of the stent graft to shafts 138, 140, 142. As shown in FIG. 7A, prosthesis portion holder 150B at distal end 148 of inner shaft 142 engages the distal end 166 of stent graft 122. Holders 150, 150A at distal ends 144, 144A of outer and intermediate shafts 138, 140 engage proximal end 168 and central turn 132 of stent graft 122, respectively. One or more of shafts 138, 140, 142 may be braided to enhance torquing stiffness to aid rotation.

Figure 6C:
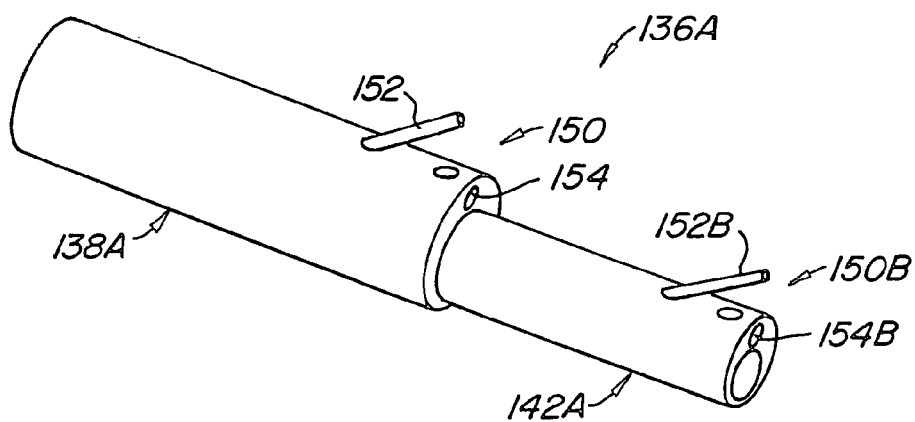
FIG. 6C is an embodiment similar to the catheter of FIG. 6A but including only inner and outer shafts.

FIG. 6C illustrates the distal end of a catheter 136A including only two shafts, outer shaft 138A and inner shaft 142A. Catheter 136A is typically used when placing an endoluminal prosthesis of the type which does not have a central turn with an increased pitch, such as those of FIGS. 5, 5A, 5B and 5C, and thus does not need a catheter with an intermediate shaft.

Figure 6D:
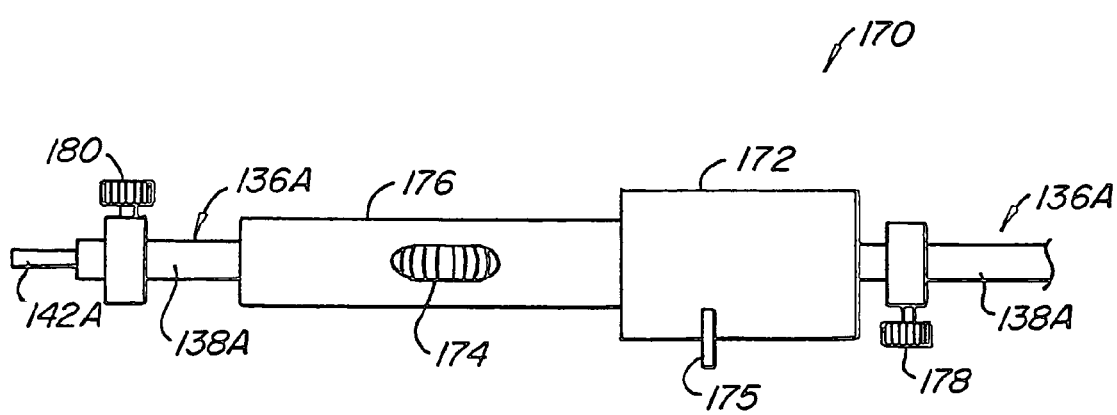
FIG. 6D illustrates a proximal end adapter mounted to the proximal end of the catheter of FIG. 6C.

FIG. 6D illustrates, in a simplified form, a proximal end adapter 170 mounted to the proximal end of catheter 136A of FIG. 6C. Proximal end adapter 170 includes distal and proximal portions 172, 176 through which catheter 136A passes. Proximal end adapter 170 provides for the rotation of either or both shafts 138A, 142A through the manipulation of thumb wheel 174 mounted to portion 176. A flip lever 175 extends from distal portion 172 and is movable between secured and released positions to either secure shafts 138A, 142A to one another or to permit shafts 138A, 142A to move axially relative to one another. Pull wires 152, 152B are normally secured to their respective shafts 138A, 142A by deployment knobs 178, 180; pulling on deployment knobs 178, 180 releases pull wires 152, 152B, respectively to permit the pull wires to be pulled to release the endoluminal prosthesis from the appropriate holder 150, 150B.

Figure 6E:
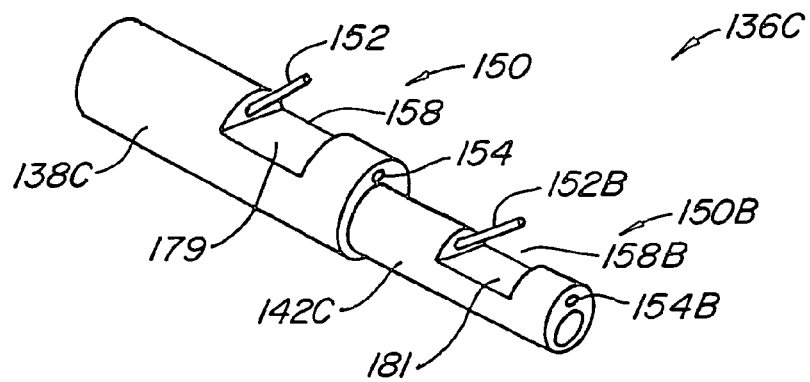
FIG. 6E illustrates an alternative embodiment of the catheter of FIG. 6C.
Figure 6F:
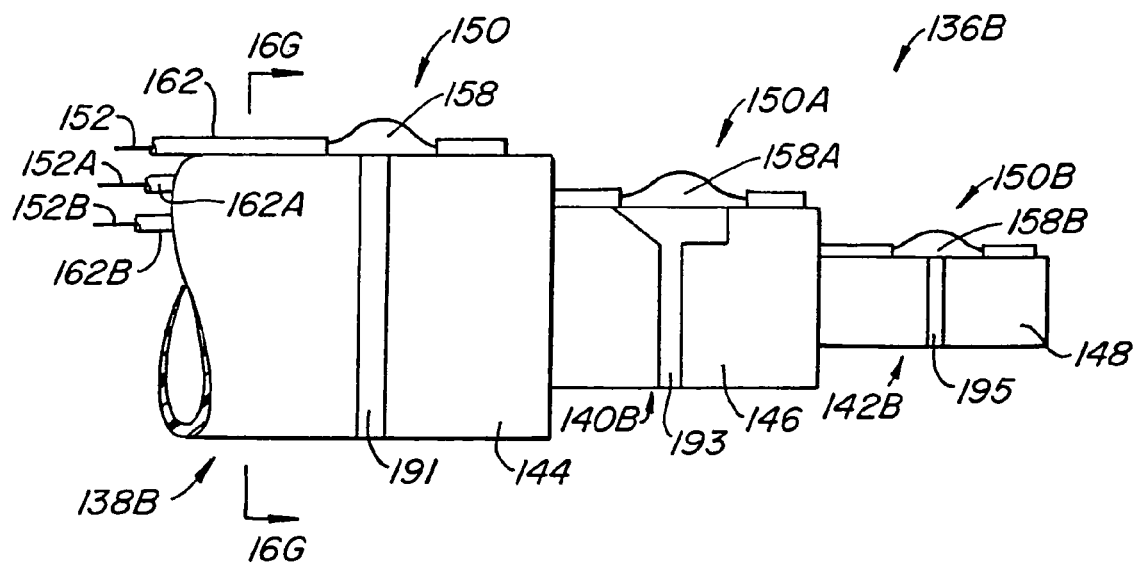
FIGS. 6F and 6G are simplified side and cross-sectional views of a further alternative embodiment of the catheter of FIGS. 6A and 6B.
Figure 6G:
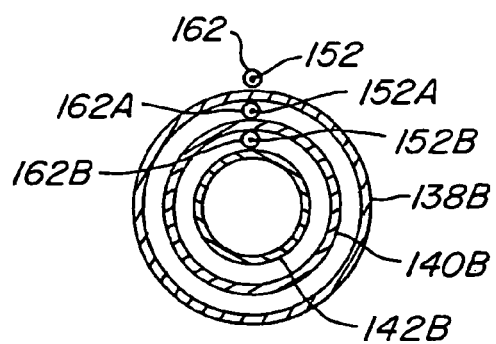

FIGS. 6F and 6G illustrate a further three-shaft embodiment of the invention similar to the three-shaft embodiment of FIGS. 6A and 6B. Instead of using lumens 154 to house pull wires 152, tubular members 162, 162A, 162B, typically hypotubes, could be secured to the outside of the shafts 138B, 140B, 142B. Gaps or breaks are provided at the distal ends of hypotubes 162, 162A, 162B to define the gaps 158, 158A, 158B.

Figure 8:
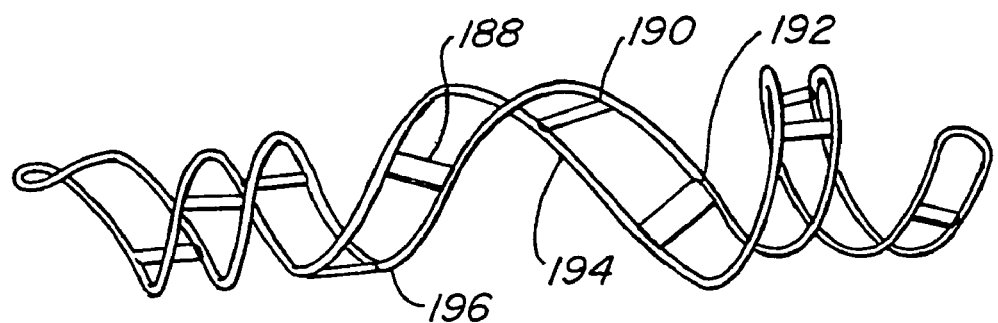
FIGS. 8 and 9 illustrate the placement of radiopaque marks at different positions along a coiled ladder-type stent having a central turn with a greatly increased pitch.
Figure 9:
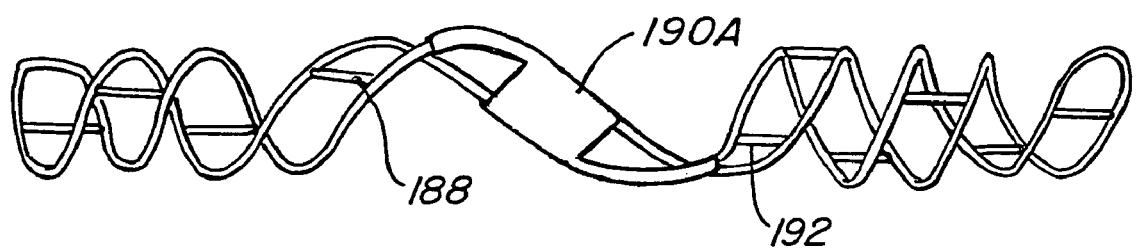

FIG. 7A shows stent graft 122 of FIG. 3 tightly wrapped about catheter 136. Distal end 166, proximal end 168 and central turn 132 of stent graft 122 are secured to distal ends 148, 144 and 146 of inner, outer and intermediate shafts 142, 138 140 by prosthesis portions holders 150. Stent graft 122 is housed within a main vessel 182 with central turn 132 aligned with the intersection 184 of main vessel 182 and branching vessel 186. To help ensure proper placement of central turn 132 at intersection 184, stent graft 122 has one or more remote visualization markers at or adjacent to turn 132. Radiopaque markers 188, 190 192 are shown in FIG. 8 at distal, intermediate and proximal portions of the central turn 194 of stent 196. Radiopaque markers may be shaped to provide information as to both location and orientation of stent 196 on the catheter. For example, radiopaque marker 190A of FIG. 9 has a broad central portion 190B extending between rail elements 110 and arm portions 190C extending along rail elements 110; this permits marker 190A to provide both location and orientation information about stent 196A. Orientation marker 190A is configured so that the viewer can determine whether the turn is facing the viewer or is away from the viewer based upon the marker's orientation. Various other marker shapes to provide both location and orientation can also be used.

Figure 10:
FIG. 10 illustrates one example of a radiopaque marker shaped to permit the determination of the orientation of the prosthesis as well as its location.

Radiopaque markers may also be used on the placement catheter itself. For example, radiopaque markers 191, 193, 195 are used on shafts 138B, 140B, 142B aligned with their respective holders 150, 150A, 150B, as shown in FIG. 6F, to indicate the location of the holders. Radiopaque marker 193 is shown to be configured as an orientation specific marker to help in the proper placement of the prosthesis. FIG. 10 illustrates the shape of an orientation-specific radiopaque marker 197 which could be placed, for example, on shafts 138, 140, 142 at one or more of the holders 150 of the embodiments of FIGS. 6A, 6C and 6E. Radiopaque or other remote visualization markers may also be used at other positions along the endoluminal prosthesis, such as at each end, or along the placement catheter.

FIG. 7B illustrates the release of proximal end 168 of stent graft 122 while FIG. 7C illustrates the subsequent release of distal end 166 of stent graft 122. It should be noted that central turn 132 remains secured to intermediate shaft 140 while the distal and proximal ends 166, 168 of stent graft 122 are released to ensure that the open region of central turn 122 remains facing intersection 184 to help ensure substantially unrestricted fluid flow between main vessel 182 and branching vessel 186. It should also be noted that prior to releasing the stent graft, the number of turns can be increased or decreased by the relative rotation of shafts 138, 140 and 142. Also, the length of stent graft 122 can be changed by the relative axial sliding motion among outer, intermediate and inner shafts 138, 140, 142. For example, instead of simply releasing proximal end 168 of stent graft 122 to the position shown in FIG. 7B, it may be desired to rotate outer shaft relative to intermediate shaft 140, keeping intermediate and inner shafts 140, 142 stationary so to unwind the proximal half of the stent graft to ensure that the stent graft is properly positioned prior to releasing the stent graft. Similarly, both outer shaft and inner shafts can be rotated while maintaining intermediate shaft stationary to create the expanded diameter condition of FIG. 7 prior to releasing any portion of the stent graft. In this way the physician can ensure that stent graft 122 is properly positioned, especially with respect to central turn 132. If necessary or desired, intermediate shaft 140 could be, for example, rotated relative to outer and inner shafts 138, 142 to help properly position or reposition central turn 132.

FIG. 7A also shows how by properly selecting the angle of connector elements 112 relative to side elements 110 for a placement catheter of a particular outside diameter, connector elements 112, indicated by dashed lines in FIG. 7A, will lie generally parallel to the axis of stent graft 122. This permits connector element 112 to lie closer to catheter 136, to provide a much smoother wrap when in its contracted, reduced-diameter state, than would result if connector elements were not generally parallel to the axis in such a state. This axial orientation can be contrasted with the off-axis orientation of connectors 112 when in the expanded diameter state of FIG. 7C. The smoother outer surface of stent graft 122 enhances the ease of insertion of the stent graft within a hollow body organ, such as blood vessel 182.

Figure 7E:
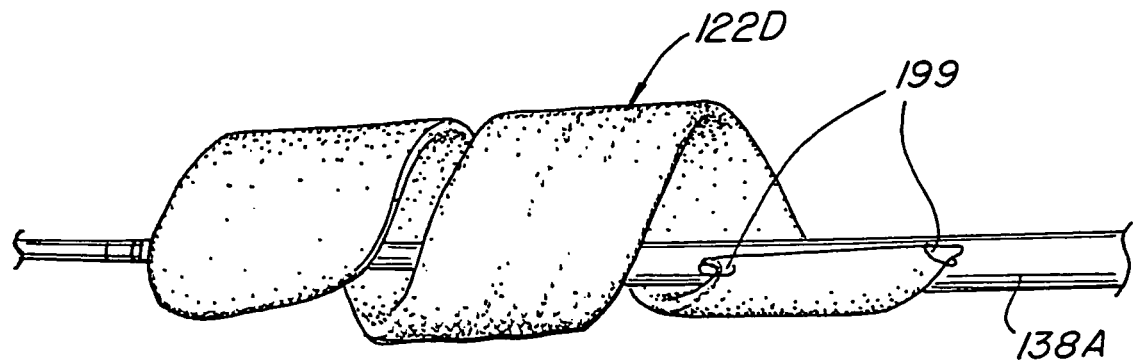
FIG. 7E illustrates the stent graft of FIG. 7D with the distal end of the stent graft released from the catheter and the proximal end of the stent graft releasably secured to the catheter at two positions.
Figure 7D:
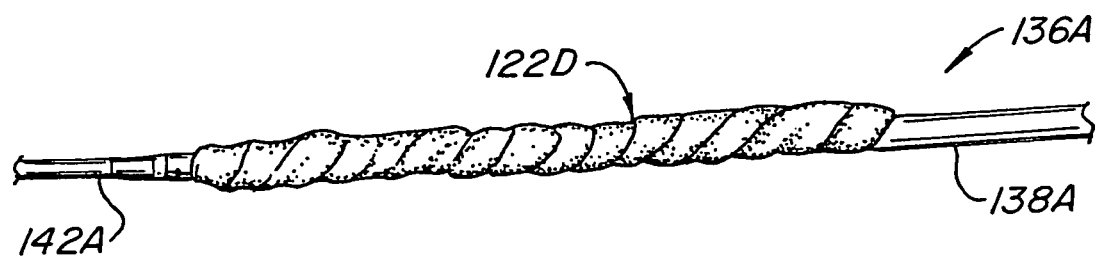
FIG. 7D illustrates the stent graft of FIG. 5C tightly wrapped about a placement catheter.

FIG. 7D illustrates stent graft 122D of FIG. 5C tightly wrapped about placement catheter, 136A of FIG. 6C with the proximal end of stent graft 122D secured to outer catheter shaft 138A and the distal end of stent graft 122D secured to inner catheter shaft 142A. FIG. 7E illustrates the structure of FIG. 7D after pull wire 152B has been pulled to release the distal end of stent graft 122D. Soon thereafter pull wire 152 will be pulled to release the proximal end of stent graft 122D from outer catheter shaft 138A. Because of the width of each turn of stent graft 122D, each pull wire 152, 152B passes through two positions 199 along an end of stent graft 122D to ensure that the stent graft lies tightly against catheter 136A during delivery.

As discussed above, stent graft 122D is placed in a radially contracted condition by rotating inner and outer catheter shafts 138A, 142A relative to one another. Once in position for deployment, catheter shafts 138A, 142A are rotated relative to each other to open stent graft 122D. Shafts 138A, 142A can also be moved longitudinally (axially) relative to one another to allow one to change the pitch and ensure that edges 135 of turns 137 of stent graft 122 will be adjacent to one another when fully deployed, as is often desired. At any point the operator can decide to retighten stent graft 122D, placing it in a radially contracted condition, to reposition the stent graft or change the pitch so long as pull wires 152, 152B have not been removed from the ends of the stent graft. Proper placement of the graft 122D, including ensuring that the edges lie adjacent to one another, can be aided by the used of radiopaque markers 121. See FIG. 1E.

Figure 11:
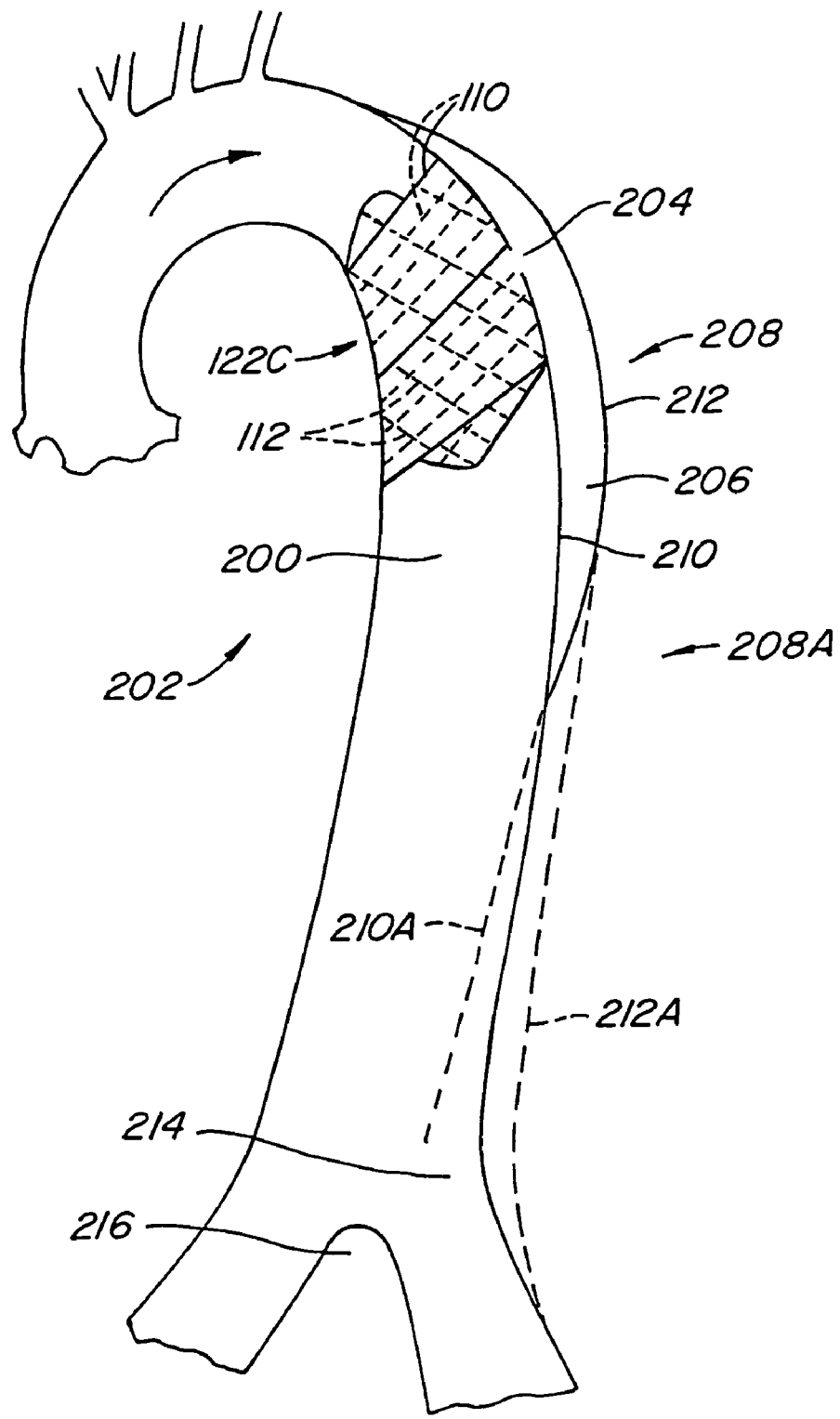
FIG. 11 illustrates of the stent graft of FIG. 5B within the true lumen of the aortic arch at the entry of an aortic dissection, an alternative aortic dissection being shown in dashed lines.

FIG. 11 illustrates the placement of stent graft 122C within the true lumen 200 of an aortic arch 202 so to cover the entry 204 into a false lumen 206 created by an aortic dissection 208. Aortic dissections are of various type but all include a false lumen caused by separation of the lining, such as intimal lining 210, from the remainder of the wall, such as wall 212 of the hollow body structure, together with an entry formed through the separated lining into the false lumen. Aortic dissections, as well as other dissections, may be of the type with a single entry 204 or may include, for example, an entry and an exit. An alternative dissection 208A is suggested by the dashed lines in FIG. 11 indicating an extension of aortic dissection 208 from the solid line portion down to an exit 214 adjacent bifurcation 216. While it may be possible to close both entry 204 and exit 214 using one or more stent grafts, it may not be necessary or desirable. Also, it may not be necessary to cover either the entrance and/or any exit to a false lumen with the stent graft to effectively treat the dissection. Stent graft 122C also has dashed lines indicating the locations of rail elements 110 and connector elements 112 of the stent.

Stent graft 122C is used with a thoracic level aortic dissection. Stent grafts may be used with dissections at other levels along aorta 218, such as at the abdominal level 220 or along the arch 222. When a stent graft is used at arch 222, or at other hollow body regions with one or more branches, stent grafts having one or more enlarged gaps, see FIGS. 3, 4 and 7C, may be used to help prevent obstruction of the branching vessel.

Stent grafts, such as those of FIGS. 5B and 5C, may be used to help repair various dissections other than aortic dissections. In particular, such stent grafts may be used for other types of vascular dissections and dissections in other hollow body organs within which dissections may be found. The dissections may be created as a result of non-penetrating trauma or invasive trauma as well as biological reasons, such as disease, stress, congenital disorders, etc.

Figure 12:
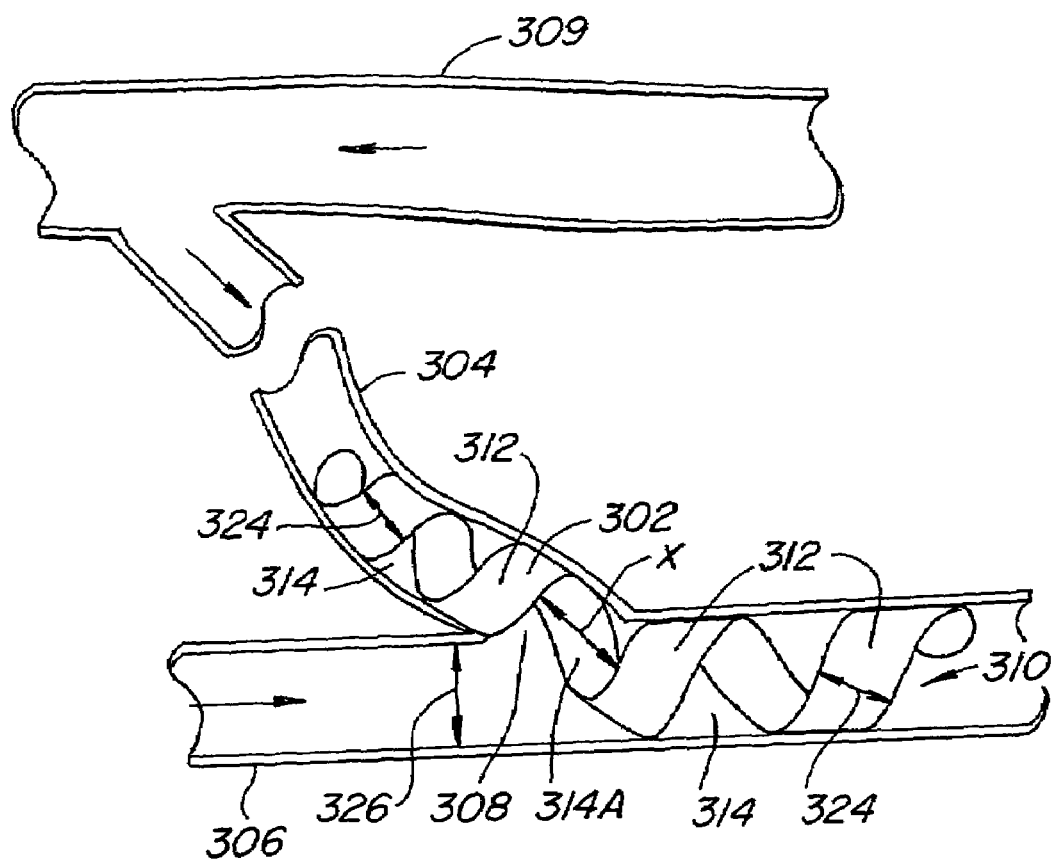
FIG. 12 is a side, partial cross-section view illustrating the venous end of an AV fistula with a stent graft extending from the AV fistula into the vein.

FIG. 12 illustrates the venous end 302 of an AV fistula 304 joined to a vein 306 at a junction 308. The opposite end of AV fistula 304 is connected to an artery 309. The construction of AV fistula 304 and the connections to artery 309 and vein 306 are conventional.

Figure 13:
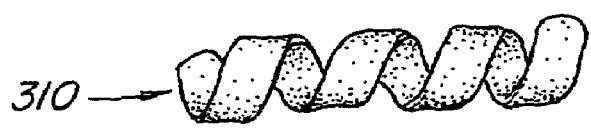
FIG. 13 illustrates the stent graft of FIG. 12 prior to placement into the AV fistula and vein.
Figure 15:
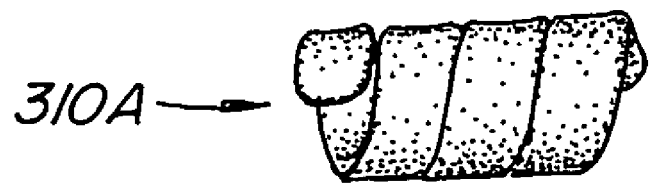
FIG. 15 illustrates a further alternative embodiment of the stent graft of FIG. 13 in which the turns are adjacent to one another.

To help treat and/or prevent the obstruction or blockage (not shown) at junction 308, an endoluminal prosthesis in the form of a coiled stent graft, such as stent graft 310, is placed so that it extends within the venous end 302 of AV fistula 304 and within vein 306 so that stent graft 310 spans both sides of junction 308. Stent graft 310 is typically of a type in which the turns 312 are generally evenly spaced apart from one another by gaps 314. While turns 312 of stent graft 310 may be evenly spaced when in a freely-expanded condition, as in FIG. 13, when placed within fistula 304 and vein 306, the gaps may not be the same from turn to turn. For example, FIG. 12 illustrates the situation in which gap 14A at junction 308 is somewhat larger than the other gaps 314. In some situations it may be desirable to use a stent graft 310A, shown in FIG. 15, in which the turns are adjacent to one another so that even at junction 308, turns 312 would be adjacent or closely spaced to effectively block fluid flow along vein 306 on one side of junction 308, that is the upstream (left) side in FIG. 12.

A typical AV fistula 304 has an inside diameter of about 4–10 mm and a length of about 2–10 cm. Stent graft 310 would typically have a slightly larger freely-expanded outside diameter such as 5 mm for a 4 mm diameter AV fistula. The length of stent graft 310 typically depends upon the length of the AV fistula and whether the stent graft is to extend into one or both of vein 306 and artery 309. Thus, the length of stent graft 310 may range from, for example, 1 cm to over 10 cm.

Figure 14:
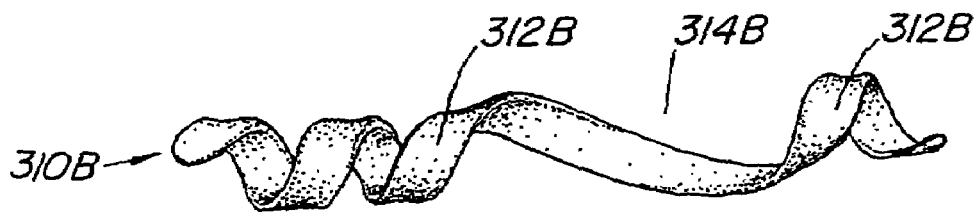
FIG. 14 illustrates an alternative embodiment of the stent graft of FIG. 13 in which the pitch between two adjacent turns is substantially greater than the pitch between other of the turns to help prevent restriction to fluid flow along the vein at the junction of the AV fistula.

Instead of the evenly spaced turns 312 of stent graft 310 of FIGS. 1 and 2, a stent graft 310B, see FIG. 14, could be used in which an extended gap 314B is provided between to adjacent turns 312B. Stent graft 310B may find particular use with gap 314B positioned at junction 308 to help ensure minimal restriction to fluid flow along vein 306 as well as from AV fistula 304 into vein 306.

A stent graft, having three sections with closely-spaced turns at the end sections and one or more loosely-spaced turns at the intermediate section, may be used. This embodiment may be used, for example, with one end section within fistula 304, the intermediate section at junction 308 and the other end section within vein 306. In addition, while the stent graft is typically a unitary item, it may be desirable to make the stent graft from two or more stent graft segments. For example, the stent graft could include three relatively short stent graft segments, one for placement in AV fistula 304, one for placement at junction 308 and one for placement along vein 306.

In the preferred embodiments stent grafts 310, 310A and 310B are made by covering wire stent blanks 316 (see FIG. 16) with a suitable graft material 315, such as ePTFE Dacron® polyester, polyurethane or natural vein. Stent blanks 316 may be made of, for example, a temperature sensitive, shape memory alloy which tends to assume a radially extended position when at body temperature. Other means for expanding stent graft 310, such as or the application of an electric current or other energy source to heat the stent, or the use of simple spring stents, may also be used.

Figure 16:
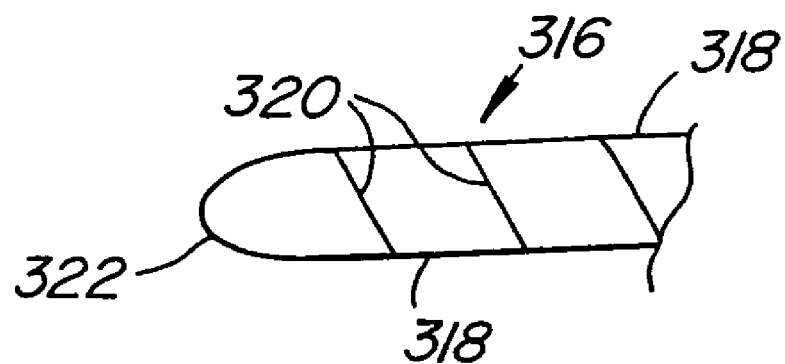
FIG. 16 illustrates the flattened end of the stent graft of FIG. 13 with the graft material removed to illustrate the stent.
Figure 17:
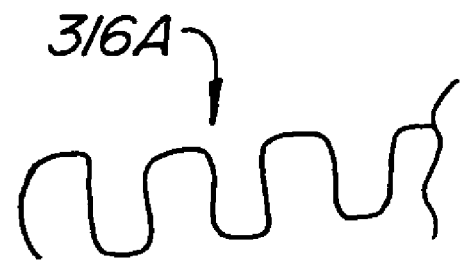
FIG. 17 illustrates an alternative embodiment of the stent of FIG. 16.

FIG. 16 illustrates one end of a stent blanks 316, used to create stent grafts 310, 310A and 310B, prior to covering stent blanks 316 with ePTFE graft material. Stent blanks 316 comprises a pair of rails 318 connected by connectors 320, rails 318 being joined at their ends to form blunt ends 322. Blunt ends 322 are configured and constructed so to minimize trauma to patient tissue. Other types of stent structures may be used. For example, the angled connectors 320 of FIG. 16 could be replaced by one or more of perpendicular connecting elements, x-shaped connector elements, undulating connector elements or any of a variety of connector elements. Also, rails 318 could be discontinuous, which would occur, for example, when stent blanks 316 is made of wire formed into a series of deep undulations, such as illustrated in FIG. 17. Other types of coiled stent structures made of a variety of biocompatible materials can be used as well. In the above-described preferred embodiments, the entire stent blank is covered with, that is encased within, graft material. In some situations it may not be necessary or desirable to cover the entire stent blank with graft material. Also, the stent blank may not have a constant width and the stent graft may have a diameter which changes over its length.

Stent graft 310 may be constructed to carry a biologically active agent, in particular a thrombolytic agent. See the discussion above with regard to FIGS. 3–5I. The thrombolytic agent may be tPA, Reteplase (generic for Retavase®), or Urokinase, or a combination of these or other thrombolytic agents to help prevent or at least reduce any thrombosis that may result from the use of stent graft 310. One or more anti-restenotic (or other anti-proliferative) agents, such as rapamnycin, taxol, and NO generators such as SNP (sodium nitroprusside), may be used in conjunction with one or more thrombolytic agents to help prevent restenosis associated with the use of stent graft 310. Other biologically active agents may also be used in conjunction with the one or more thrombolytic agents alone or in conjunction with one or more anti-restenotic agents.

In use stent graft 310 may be placed into vein 306 when AV fistula 304 is initially grafted between the artery and vein. However, in the usual case stent graft 310 would not be used until the formation of some blockage at junction 308 has been observed. After any necessary removal of the blockage, stent graft 310 can be mounted to a suitable placement catheter, such as one disclosed in U.S. Pat. No. 6,238,430 B1. With stent graft 310 tightly wrapped about the placement catheter, the placement catheter is advanced percutaneously into vein 306, and then into venous end 302 of AV fistula 304. Proper longitudinal and rotary placement of stent graft 310 can be monitored using remote visualization techniques, which may or may not involve the use of radiopaque markers carried by the stent graft. Radiopaque markers, when used, would likely be used at the ends of stent graft 310 and/or at the turn or turns 312 expected to be at or adjacent to junction 308 to help ensure proper placement. Once in position, stent graft 310 is released from the placement catheter and is expanded to the position of FIG. 12.

To help eliminate any substantial hindrance to fluid flow along vein 306, stent graft 310 may be selected and placed so that the turns 312 at junction 308 are separated by a distance X. However, future testing may indicate that in some, or possibly all, cases it may be desirable to have turns 312 at junction 308 be positioned adjacent one another to eliminate gap 14A and thus prevent fluid flow through the vein on the upstream (left) side of the junction.

Other modification and variation can be made to the disclosed embodiments without departing from the subject of the invention as defined in the following claims. For example, stent graft 310 could be a bifurcated, generally Y-shaped stent graft.

Any and all patents, applications, and printed publications referred to above are incorporated by reference.

What is claimed is:

1. A method for enhancing the function of an AV fistula comprising:
    selecting an endoluminal prosthesis comprising a coiled body and a graft material at least partly covering the coiled body to create a coiled stent graft with generally helically-extending turns, said turns having an average width;
    said selecting step comprising choosing an endoluminal prosthesis carrying a thrombolytic agent; and
    placing the stent graft within an AV fistula and optionally within at least one blood vessel to which the AV fistula is connected, said thrombolytic agent helping to reduce any thrombosis associated with the stent graft.

2. The method according to claim 1 wherein the choosing step is carried out wit the chosen endoluminal prosthesis also carrying a non-thrombolytic biologically active agent.

3. The method according to claim 1 wherein the choosing step is carried out with the chosen endoluminal prosthesis also carrying an anti-restenotic agent.

4. The method according to claim 3 wherein the choosing step is carried out with the anti-restenotic agent: on the surface of the graft material, on the surface of the coiled body, incorporated into the graft material to create an anti-restenotic agent/graft material matrix, or an appropriate combination thereof.

5. The method according to claim 3 wherein the choosing step is carried out with the anti-restenotic agent comprising at least one of rapamycin, taxol, and SNP (sodium nitroprusside).

6. The method according to claim 1 wherein the placing step is carried out with the stent graft placed within the AV fistula and at least one blood vessel so the stent graft extends across the junction between the AV fistula and the at least one blood vessel.

7. The method according to claim 6 wherein the selecting and placing steps are carried out so that the turns of the stent graft at the junction are spaced-apart from one another so as to not block fluid flow through the blood vessel.

8. The method according to claim 6 wherein the selecting and placing steps are carried out so that the turns of the stent graft at the junction are next to one another so to effectively block fluid flow along the blood vessel on one side of the junction.

9. The method according to claim 1 wherein the placing step is carried out with the stein graft placed within the AV fistula and a vein.

10. The method according to claim 1 wherein the choosing step is carried out with the thrombolytic agent on the surface of the graft material.

11. The method according to claim 1 wherein the choosing step is carried out with the thrombolytic agent on the surface of the coiled body.

12. The method according to claim 1 wherein the choosing step is carried out with the thrombolytic agent incorporated into the graft material to create a thrombolytic agent/graft material matrix.

13. The method according to claim 1 wherein the choosing step is carried out with the thrombolytic agent: on the surface of the graft material, on the surface of the coiled body, incorporated into the graft material to create a thrombolytic agent/graft material matrix, or an appropriate combination thereof.

14. The method according to claim 1 wherein the choosing step is carried out with the thrombolytic agent comprising at least one of tPA, Reteplase and Urokinase.

15. The method according to claim 1 wherein the choosing step is carried out with a delay-release material associated with the thrombolytic agent to delay the release of the thrombolytic agent.

16. The method according to claim 15 wherein the choosing step is carried out with the delay-release material comprising a biodegradable, delay-release layer.

17. The method according to claim 1 wherein the choosing step is carried out with the thrombolytic agent microencapsulated using a biodegradable encapsulation material so as to delay migration of said thrombolytic agent from said prosthesis.

18. A method for enhancing the function of an AV fistula comprising:
    selecting an endoluminal prosthesis comprising a coiled body, a graft material at least partly covering the coiled body and a thrombolytic agent carried by at least one of the coiled body and the graft material, so to create a coiled stent graft with generally helically-extending turns;
    placing the stent graft within an AV fistula and an associated vein so the stent graft extends across the junction between the AV fistula and the vein, said thrombolytic agent helping to reduce any thrombosis associated with the stent graft;
    the selecting and placing steps being carried out so that the turns of the stent graft at the junction are separated by a gap so to not block fluid flow along the vein.

19. A thrombolytic AV fistula assembly comprising:
    an artificial AV fistula comprising a tubular body having a venous end and an arterial end;
    a coiled stent graft comprising a coiled body, a graft material at least partially covering the coiled body, and a thrombolytic agent carried by at least one of the coiled body and the graft material;
    the coiled stent graft having generally helically-extending turns, said turns having edges; and
    the stent graft housed partially within the AV fistula at at a chosen one of venous and arterial ends so to be extendable into a corresponding vein or artery, said thrombolytic agent helping to reduce any thrombosis associated with the stent graft.

20. The assembly according to claim 19 wherein said edges of adjacent turns are adjacent to one another.

21. The assembly according to claim 19 wherein at least some of the turns are spaced-apart by gaps so that said spaced-apart turns do not overlap one another.

22. The assembly according to claim 21 wherein the gaps are generally equal in length.

23. The assembly according to claim 21 wherein the lengths of the gaps vary by more than 100%.

24. The assembly according to claim 19 wherein the coiled body comprises a framework of lateral rails and connectors.

25. The assembly according to claim 19 wherein the graft material is synthetic graft material.

26. The assembly according to claim 25 wherein the synthetic graft material is expanded PTFE.

27. The assembly according to claim 19 wherein the thrombolytic agent is on the surface of the graft material.

28. The assembly according to claim 19 wherein the thrombolytic agent is on the surface of the coiled body.

29. The assembly according to claim 19 wherein the thrombolytic agent is incorporated into the graft material to create a thrombolytic agent/graft material matrix.

30. The assembly according to claim 19 wherein the thrombolytic agent is: on the surface of the graft material, on the surface of the coiled body, incorporated into the graft material to create a thrombolytic agent/graft material matrix, or an appropriate combination thereof.

31. The assembly according to claim 19 wherein the thrombolytic agent comprises at least one of tPA, Reteplase and Urokinase.

32. The assembly according to claim 19 further comprising a delay-release material associated with the thrombolytic agent to delay the release of the thrombolytic agent.

33. The assembly according to claim 32 wherein the delay-release material comprises a biodegradable, delay-release layer.

34. The assembly according to claim 19 wherein the thrombolytic agent is microencapsulated using a biodegradable encapsulation material so as to delay migration of said thrombolytic agent from said prosthesis.

35. A thrombolytic AV fistula assembly comprising:
- an artificial AV fistula comprising a tubular body having a venous end and art arterial end;
- a coiled stent graft comprising a coiled body, a graft material at least partially covering the coiled body, and a thrombolytic agent carried by at least one of the coiled body and the graft material, the turns of the coiled stent graft being generally helically-extending and spaced-apart by gaps;
- the lengths of the gaps varying by more than 100%; and
- the stent graft housable partially within the AV fistula and extending past at least one of the venous and arterial ends, said thrombolytic agent helping to reduce any thrombosis associated with the stent graft.

* * * * *